United States Patent [19]
Welebir

[11] 4,333,758
[45] Jun. 8, 1982

[54] 1-TRIACONTANOL PLANT GROWTH STIMULATOR FORMULATIONS

[76] Inventor: Andrew J. Welebir, 1008 Steeples Ct., Falls Church, Va. 22046

[21] Appl. No.: 146,005

[22] Filed: May 2, 1980

Related U.S. Application Data

[63] Continuation-in-part of Ser. No. 47,696, Jun. 12, 1979.

[51] Int. Cl.³ ............................................. A01N 59/00
[52] U.S. Cl. ........................................... 71/80; 71/89; 71/92; 71/96; 71/115; 71/117; 71/122
[58] Field of Search ...................... 71/122, 80, 77, 65, 71/97

[56] References Cited

U.S. PATENT DOCUMENTS

| 1,703,362 | 2/1929 | Popoff | 71/65 |
| 2,558,762 | 7/1951 | Kohr, Jr. et al. | 71/65 |
| 3,630,717 | 12/1971 | Miller | 71/122 |
| 3,756,801 | 9/1973 | Herschler | 71/65 |
| 4,150,970 | 4/1979 | Ries et al. | 71/122 |
| 4,169,716 | 10/1979 | Ashmead | 71/122 |
| 4,169,717 | 10/1979 | Ashmead | 71/77 |
| 4,230,485 | 10/1980 | Ohlrogge | 71/122 |

OTHER PUBLICATIONS

R. Hertel et al., Planta (Berl.), 107, 325–340, (1972).
Peter M. Ray, et al., Plant Physiol., (1977) 59, 357–364; 60, 585–591.
B. W. Poovaiah et al., Plant Physiol., (1976), 58, pp. 783–785.
B. W. Poovaiah et al., Plant Physiol., 54, 289–293, (1974).
Carl Leopold, Plant Growth Regulators, 33–41, (1977).
Leopold et al., Plant Growth Substances, 780–788, (1974).
Robert S. Bandurski, Plant Growth Substances, 1–17, (1979).

Primary Examiner—Glennon H. Hollrah
Attorney, Agent, or Firm—Birch, Stewart, Kolasch & Birch

[57] ABSTRACT

A plant growth stimulator formulation including a substantially water soluble concentrate solution of 1-triacontanol, a polar organic solvent and metal ions.

16 Claims, 2 Drawing Figures

1-TRIACONTANOL PLANT GROWTH STIMULATOR FORMULATIONS

CROSS-REFERENCE TO RELATED APPLICATIONS

This application is a continuation-in-part of copending U.S. application Ser. No. 47,696, filed on June 12, 1979.

BACKGROUND OF THE INVENTION

1. Field of the Invention

The present invention relates to a chemical composition which, when applied to growing plants, is effective in stimulating plant growth. More particularly, the present invention is directed to a chemical formulation of 1-triacontanol in combination with a polar organic solvent, metal ions and water, with water being present as the major constituent.

2. Description of the Prior Art

Recently, 1-triacontanol $CH_3(CH_2)_{28}CH_2OH$ has been under investigation as a naturally occurring plant growth stimulant [see S. K. Ries, et al, Science, 195 1339 (1977)]. In fact, field trails are presently being conducted in an attempt to optimize the conditions at which a chemical formulation of this compound can be applied to plants.

In the research which is presently being conducted utilizing 1-triacontanol as a plant growth regulator, use is being made of a relatively large amount of surfactants in the chemical formulation in an effort to render the 1-triacontanol soluble in water. As is well known, 1-triacontanol is basically insoluble in water. Of course, the use of a large amount of water is imperative in order to economically and effectively apply the chemical formulation to large areas of growing plants. Accordingly, it is imperative to render the 1-triacontanol water soluble so that it can be properly disbursed in a large quantity of water which is to be subsequently applied to the plants. However, the organic solvents which are presently being utilized to make the 1-triacontanol soluble in water, for example, the use of certain chemicals such as chloroform and chemical surfactants and also the use of other water insoluble solvents, have been found to be detrimental to both plant life and to the environment. Thus, it has been found, for example that the use of surfactants coats the plant, thereby preventing entry of the 1-triacontanol into the plant and, consequently, the plant growth properties of the 1-triacontanol are rendered less effective.

It is known that calcium can alter the effects of plant hormones including indole acetic acid (IAA). Other cations have also been found to effect plant growth and to affect the effects of plant growth regulators. The following cations have the ability to increase auxin binding to the cell membrane and inhibit IAA-stimulated growth in the order

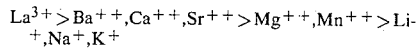

(Pooviah and Leopold, Plant Physiology (1976), Vol. 58, p. 182-185.)

IAA is known to rapidly stimulate cell elongation and enlargement, a process that involves loosening of the cell wall. IAA occurs primarily in esterified form, the myo-inositol ester comprising about fifty percent in Zea Mays. Only about one to ten percent of the relatively large amount of IAA present compared to other plants occurs as fee IAA. Auxin binding to cell membranes is a reversible process with a $K_m$ between $10^{-6}$ and $5 \times 10^{-5}$ M, and there are apparently two binding sites. Site 1 binds both active and inactive auxin analogs while site 2 appears to be auxin specific.

SUMMARY OF THE INVENTION

Accordingly, an object of the present invention is to provide an inexpensive and effective means for formulating 1-triacontanol without the use of surfactants or other large quatities of organic solvents which have been found to adversely affect plant growth.

Another object of the present invention is to provide a chemical formulation which contains a polar organic solvent which renders 1-triacontanol soluble in water and at the same times poses no threat to plant life or to the environment.

Pursuant to the present invention, the above problems have been eliminated by providing a chemical formulation which can be used with water for application to plant life. According to the present invention, 1-triacontanol is dissolved in a polar organic solvent, in an amount sufficient to form a water soluble concentrate. Typically, the concentrate can be formed by mixing together one part by weight (grams) of 1-triacontanol with up to about 5,000,000 parts by volume (ml) of the polor organic solvent, preferably between 1 and 500,000 ml of polar organic solvent to one gram of 1-triacontanol, more preferably one part by weight of 1-triacontanol to about 1,000 parts by volume of the polar organic solvent and most preferably about one part of 1-triacontanol to about 40-120 parts of solvent. The polar organic solvent can be any water soluble solvent or solvent mixture containing one or more functional groups, which renders the resulting 1-triacontanol solution soluble in water. This solution is then dissolved in a large quantity of water which contains metal salts with stirring and/or shaking.

The polar organic solvents which are utilized in the present invention to aid in the solubility of the 1-triacontanol in water include alcohols, ketones, water soluble ethers, glycols, organic carboxylic acids and any other solvent or solvent mixture containing one or more functional groups contained in any one class or classes of said solvents. Typical polar organic solvents include acetone, methyl ethyl ketone, methanol, ethanol, isopropanol, diethylene glycol, n-butanol, propylene glycol, dioxane and acetic acid.

Typical ratios of the 1-triacontanol-organic solvent solution to water may vary from 1:10,000 to 1:1 parts by volume, preferably 1:1,000 to 2:100 parts by volume, depending upon the desired concentration of the 1-triacontanol required or desired in the final solution.

In accordance with another aspect of the present invention, it has been discovered that indole-3-acetic acid, which normally stimulates plant growth, inhibits the plant growth stimulating effects of 1-triacontanol in plants. Various plant growth substances were added to triacontanol formulations in order to improve the effectiveness of the plant growth stimulating properties of the 1-triacontanol formulations. The following plant growth substances were tested: indole-3-acetic acid (IAA); gibberellic acid (GA₃); kinetin; 2,4-dichlorophenoxyacetic acid (2,4-D); 2,3,5-triiodobenzoic acid (TIBA); and maleic hydrazide (MH). Various metal salts were also tested for their effectiveness in improving the plant growth stimulating properties of the 1- triacontanol formulations. The salts tested included CaCl$_2$, LaCl$_3$, Ce(SO$_4$)$_2$, MgCl$_2$, MnCl$_2$ and mixtures thereof. It has been discovered that the presence of both 1-triacontanol and metal salts in the formulations creates a synergistic effect in increasing the plant growth stimulating properties of the formulations. Although not wishing to be bound by any specific theory as to the precise mechanism by which the invention achieves its results, the plant growth stimulating properties appear to be due to the fact that the metal ions, Ca$^{++}$ etc., increase the binding of IAA to cell membrane, and possibly make it unavailable for binding to 1-triacontanol.

It has been found that the metal ions of the metal salts are most effective when applied to the leaves by spraying at concentrations of about $10^{-1}$ Molar to $10^{-5}$ molar, preferably at concentrations of about $10^{-2}$ molar to $10^{-4}$ molar and most preferably at concentrations of between about $10^{-2}$ and $10^{-3}$ molar. Spraying should be done no earlier than the fifth day (for corn) after germination or when the plant has 2-3 true leaves for best results. The metal ions should be sprayed on the area where the plants are grown in an amount of between $10^{-4}$ and $10^{-1}$ Moles per acre, preferably in an amount of between $10^{-2}$ and $10^{-1}$ moles per acre using 10 liters/acre of the formulation.

Typically, the 1-triacontanol-polar organic solvent concentrate-water mixture is applied to the growing plants in an amount sufficient to achieve a distribution of at least 1 mg of 1-triacontanol per acre, advantageously 5 to 20 mg per acre.

The chemical formulation, according to the present invention, can be applied to plant life in any desired manner although the spraying of the growing plant life has been found to be particularly effective.

The present invention can also be carried out by applying the metal salts or aqueous solutions of the metal salts to the soil where the seeds have been planted. This is preferably done after the plants have been planted and at a time up to several hours before the plants are treated with 1-triacontanol. For example, $10^{-1}$ to $10^{-3}$ molar aqueous solutions of CaCl$_2$ can be applied to the soil at a rate of about 200 ml per plant. It is preferable that each plant receive at least about $10^{-4}$ moles of the ion. After several hours, in which time the plants have absorbed some of the metal ions, the plants can be sprayed with the 1-triacontanol solution or the 1-triacontanol can be added to the soil.

The metal salts which are useful are any salts or compounds which release metal ions in water. Inorganic metal salts are preferred.

The size of the ionic radii of the metal ions appears to be related to the effectiveness of the ions in increasing crop yield. Metal ions which have ionic radii of about between 0.60 to 1.5 angstroms are useful, metal ions with ionic radii of between 0.85 to 1.5 angstroms are preferred and metal ions with ionic radii between about 0.95 and 1.3 angstroms are most preferred.

The average ionic radii of the preferred metal ions are listed below.

| Ion | Avg. radius (Angstroms) | Ion | Avg. radius (Angstroms) |
|---|---|---|---|
| Ca$^{++}$ | 1.08 | Mn$^{++}$ | 0.88 |
| Sr$^{++}$ | 1.24 | La$^{+++}$ | 1.10 |
| Ba$^{++}$ | 1.42 | Ce$^{+4}$ | 0.94 |
| Cd$^{++}$ | 1.05 | Mg$^{++}$ | 0.77 |

-continued

| Ion | Avg. radius (Angstroms) | Ion | Avg. radius (Angstroms) |
|---|---|---|---|
| Pb$^{++}$ | 1.19 | | |

The ionic radii of other metal ions which may be used in accordance with the present invention are listed below.

| Ion | Avg. radius (Angstroms) | Ion | Avg. radius (Angstroms) |
|---|---|---|---|
| Ce$^{+++}$ | 1.034 | Pr$^{+4}$ | 0.90 |
| Cr$^{+2}$ | 0.89 | Sm$^{+3}$ | 0.964 |
| Cu$^{++}$ | 0.96 | Sm$^{+2}$ | 0.93 |
| Er$^{+3}$ | 0.881 | Tb$^{+3}$ | 0.923 |
| Eu$^{+3}$ | 0.950 | Tb$^{+4}$ | 0.84 |
| Eu$^{+2}$ | 0.950 | Ti$^{2}$ | 0.94 |
| Gd$^{+3}$ | 0.938 | Ti$^{+3}$ | 0.95 |
| In$^{+3}$ | 0.81 | Tm$^{+3}$ | 0.87 |
| Lu$^{+3}$ | 0.93 | V$^{+2}$ | 0.88 |
| Nd$^{+3}$ | 0.995 | Y$^{+3}$ | 0.893 |
| Pa$^{+5}$ | 0.89 | Yb$^{+2}$ | 0.93 |
| Pa$^{+4}$ | 0.84 | Yb$^{+3}$ | 0.858 |
| Pm$^{+3}$ | 0.979 | | |
| Pr$^{+3}$ | 1.013 | | |

Metal ions which have a positive valence of at least +2 are most effective. Salts of the alkaline earth metals such as Calcium (Ca$^{++}$), barium (Ba$^{++}$) and strontium (Sr$^{++}$) may be used with Ca$^{++}$ being preferred from this group because of its effectiveness, availability as a water soluble salt and its non-toxicity and exemption from tolerance by the Environmental Protection Agency (EPA). Other metals of Group II of the Periodic Table are also useful such as beryllium (Be$^{++}$) and magnesium (Mg$^{++}$). Metal ions from the lanthanide series are also very effective with metal ions from the lower end of the series such as lanthanum (La$^{+3}$) and cerium (Ce$^{+4}$) being preferred and La$^{+3}$ being most preferred from this series. Various metal ions of the transition metals are also useful. Of the transition metals, the Lanthanide series metals are useful as discussed above as well as other transition metals such as manganese (Mn$^{++}$).

Other useful metals include cadmium (Cd$^{++}$), lead (Pb$^{++}$) and magnesium (Mg$^{+2}$).

In summary, many different metal ions and mixtures thereof are useful in increasing plant yield when used in combination with 1-triacontanol. The effectiveness of the different metal ions is dependent upon the concentration at which they are used, the particular plant species to which they are applied and various other factors, including pH, pH 7 or greater being preferred but not required for positive results. Therefore, it is possible that other metal ions than those discussed above might be useful in stimulating plant growth in accordance with the present invention.

The metal ions which appear to be most effective are La$^{+3}$, Ca$^{++}$, Sr$^{++}$, Ba$^{++}$, Cd$^{++}$, Pb$^{++}$, Mn$^{++}$, Ce$^{++}$ and Mg$^{++}$, with La$^{+3}$ and Ca$^{++}$ showing the highest increase in crop yield and Ca$^{++}$ being most preferred because it is non-toxic and has been exempted from tolerance requirements by the EPA.

The chemical formulations of the present invention, without metal ions, when applied to field and sweet corn, sugar cane, tomatoes, cucumbers, beans, and the like, have been found to increase production in a greenhouse-controlled environment in an amount up to about 24% based upon the dry weight of the plants. Similar tests under field conditions of 1,000 acres or more have resulted in an increase in crop yield of field corn of from about 6 to 16% measured in terms of bushels per acre.

The chemical formulations of the present invention, with the added metal salts, increased the dry weight yield of sweet corn up to 72% and an average of 40-50% in a greenhouse-controlled environment as compared to the up to 20% increase obtained with the formulations having no metal salts. The formulations having the metal salts can also be expected to be effective on crops such as corn, navy beans, cucumbers, radishes, carrots, tomatoes and asparagus as well as on other various types of plants.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

BREIF DESCRIPTION OF THE DRAWING

FIG. 1 is a graph showing the relationship between the concentration of $CaCl_2$ and the increase in the plant growth stimulating effects of the formulation for sweet corn with a concentration of 1-triacontanol of 100 μg/l; and FIG. 2 is a graph showing the relationship between the concentration of $LaCl_3$ and the plant-growth stimulating effects of the formulation for sweet corn with a concentration of 1-triacontanol of 100 μg/l.

DETAILED DESCRIPTION

EXAMPLES

Figure 1:
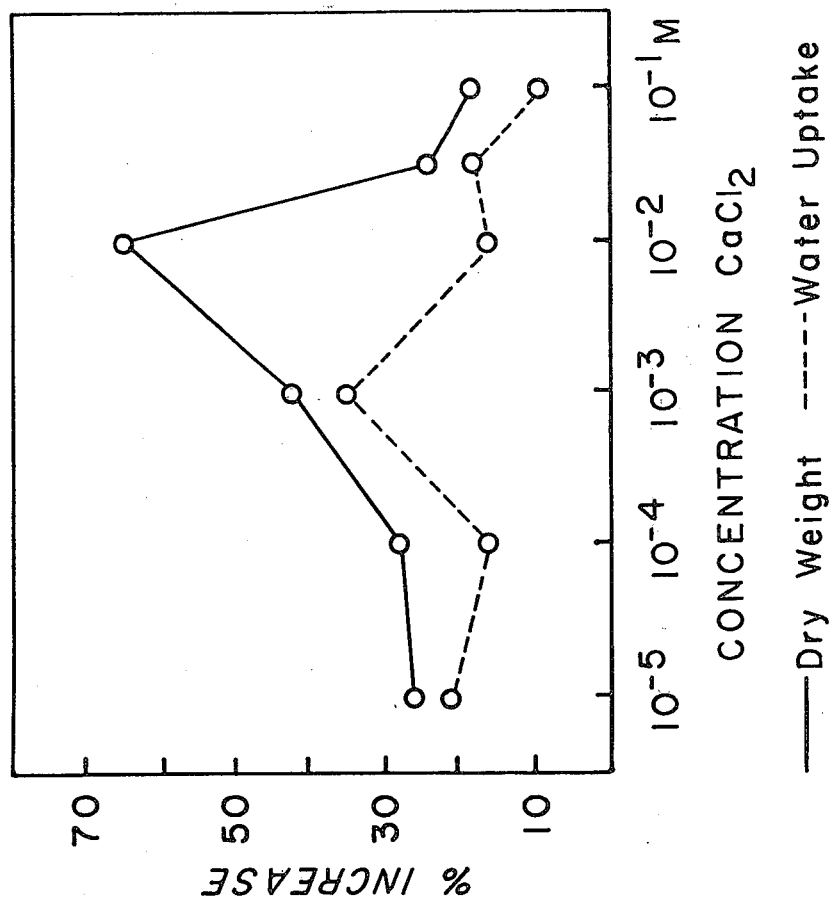
Figure 2:
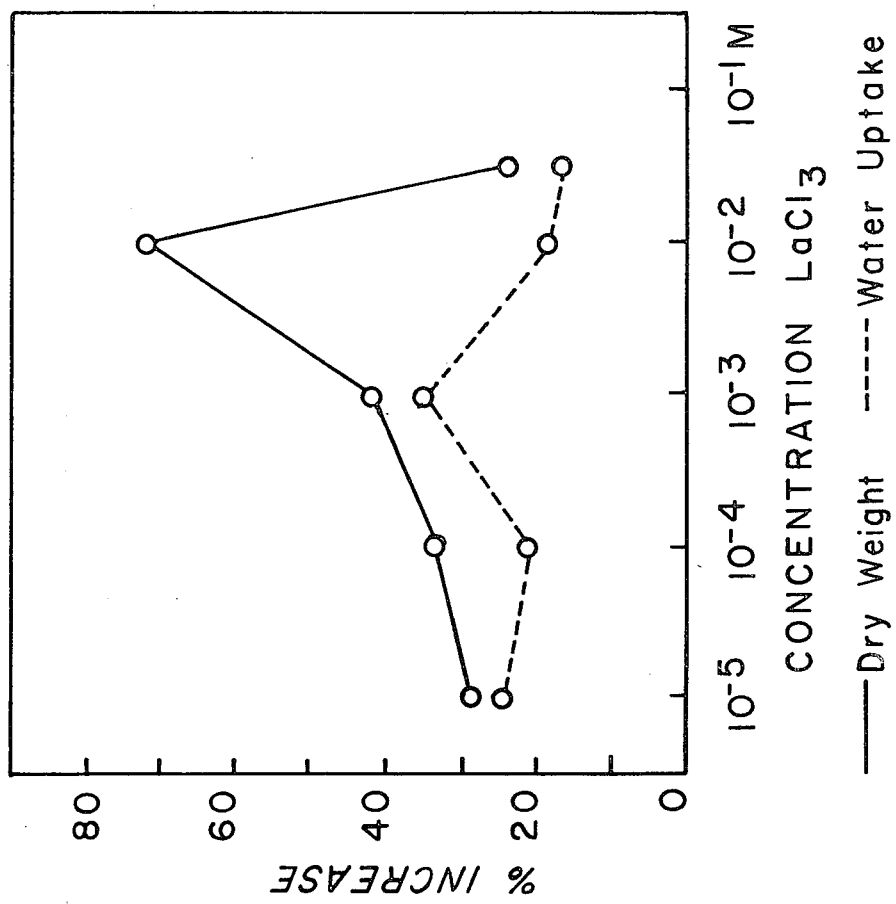

The following examples are presented herein as being exemplary of the present invention and, accordingly, should not be considered, in any way, as being limitative of the applicant's inventive contribution.

EXAMPLE 1

A 1 mg quantity of 1-triacontanol was dissolved in 10 ml of boiling acetone (or methyl ethyl ketone) and the solution was cooled to room temperature. This was added to 990 ml of water with vigorous stirring over a 30-second period. The resultant solution may be applied to plant life aerially at a concentration of 10 mg per acre using 10 liters of solution per acre. The solution may further be diluted with ten parts of water resulting in a concentration of 1 mg per acre.

EXAMPLE 2

A 10 mg quantity of 1-triacontanol was dissolved in 100 ml of methanol. The mixture was added to 900 ml of water heated to 50 degrees with vigorous stirring. The concentrate may be diluted with 9 liters of water resulting in a solution containing 1 mg per liter. This solution may be applied as described under Example 1.

EXAMPLE 3

One mg of 1-triacontanol was dissolved in 25 ml of hot isopropanel and the hot solution was poured into 975 ml of water with vigorous stirring over a one-minute period. This solution may be applied as described above under Example 1.

EXAMPLE 4

One mg of 1-triacontanol was dissolved in 25 ml of hot diethylene glycol and added to 975 ml of rapidly stirring water.
The resulting solution may be used as described above.

EXAMPLE 5

One mg of 1-triacontanol was dissolved in 10 of hot n-butanol and the mixture was added with stirring to 990 ml of water at 60 degrees. The solution was cooled to room temperature before use.

EXAMPLE 6

Ten mg of 1-triacontanol was dissolved in 100 ml of warm dioxane and added over 60 seconds to 950 ml of warm water. The solution may be used as described under Example 1.

EXAMPLE 7

One mg of 1-triacontanol was dissolved in 50 ml of hot propylene glycol and added to 950 ml of water with stirring. This solution may be used as described above.

The 1-triacontanol which can be utilized in the present invention can be that which is well known in the art. However, particularly good results are achieved when utilizing 1-triacontanol produced by the method disclosed in U.S. Pat. No. 4,167,641.

COMPARATIVE RESULTS

1-Triacontanol which had a melting point of 87° C. was prepared in accordance with the teachings of U.S. Pat. No. 4,167,641 entitled, "Synthesis of Long-Chain Carboxylic Acids and Alcohols." All solvents were of reagent grade. Hybrid sweet corn seeds (Var. "Silver Queen") were obtained from the Wetzel Seed Co., Inc., Harrisonburg, Va. Fertilizer contained 15% (w/w) nitrogen (6.8% from ammonium phosphate, 8.2% from urea), 30% phosphorus ($P_2O_5$ and ammonium phosphate), and 15% potassium ($K_2O$). Other nutrients present were copper, manganese, and zinc (from sulfates), all 0.05%, and 0.10% chelated iron.

Seeds were planted 5 cm apart (1:1 vermiculite:peat, v/v) in trays 30×60×6 cm containing 30 to 40 plants each. Each received about 300 ml of water per day. On the seventh day after shoots appeared, plants were sprayed with and without 100 μg/l of 1-triacontanol solution, with and without fertilizer. Fertilizer was applied at the same time the plants were sprayed at a concentration of 10 g/l. Eight-hour nights and sixteen-hour days (200 w/m²) were maintained at temperatures of 20° C. and 25° C., respectively.

All plants were sprayed to the drip point (approximately 100 ml of solution per tray). Plants were harvested on the fourteenth day after germination and fresh weights were obtained. Drying took place in an oven at 125° C. for a period of two hours, after which the dry weights were determined. Subtraction of the dry weights from the fresh weights gave the water uptake per plant.

A comparison study was made between the formulation of the Ries et al U.S. Pat. No. 4,150,970 and the surfactant-free formulation, of the present invention.

The following formulations were used in the Experiment:

FORMULATION 1

100 μg triacontanol was dissolved in 1 ml of chloroform and shaken with 1 liter of water containing 1 g of Tween 20 (Example II of the Ries et al, U.S. Pat. No. 4,150,970).

FORMULATION 2

100 μg of triacontanol was dissolved in 20 ml of acetone at 50° C. and the resultant solution was dissolved in 980 ml of water at room temperature.

FORMULATION 3

100 μg of triacontanol was dissolved in 50 ml of ethanol and the resultant solution was dissolved in 950 ml of water.

FORMULATION 4

100 μg of triacontanol was dissolved in 20 ml of acetone at 50° C. and the resultant solution was diluted 1:1 with water, at 50° C. and the resultant solution was diluted 1:1 with water.

FORMULATION 5

100 μg of triacontanol was dissolved in 40 ml of 1:1 acetone:water and diluted 1:1 with water.

The increases in dry weight and water uptake over the controls are reported in Tables 1-5, spraying 100 μg/l of triacontanol.

The various plant growth substances i.e., IAA, GA, Kinetin, 2,4-D, TIBA and MH and the metal ions were added to the water before mixing with the 1-triacontanol concentrate in the experiments shown in Table 5.

TABLE 1

Increases the Dry Weight of 14-Day Old Hybrid Sweet Corn ("Silver Queen") Sprayed with 100 μ/l of Triacontanol Using Different Formulations without 15-30-30 Fertilizer.

| FORMULATION | AVERAGE DRY WT. (mg/shoot) CONTROL | AVERAGE DRY WT. (mg/shoot) $C_{30}H_{61}OH$ | PERCENT INCREASE IN DRY WT. | LEVEL OF SIGNIFICANCE |
|---|---|---|---|---|
| 1 | 179 | 181 | +1% | N.S. |
| 2 | 190 | 210 | +11% | .01 |

TABLE 2

Increases in Dry Weight of 14-Day Old Hybrid Sweet Corn ("Silver Queen") Sprayed with 100 μg/l Triacontanol Using Different Formulations with 15-30-15 Fertilizer.

| FORMULATION | AVERAGE DRY WT. (mg/shoot) CONTROL | AVERAGE DRY WT. (mg/shoot) $C_{30}H_{61}OH$ | PERCENT INCREASE IN DRY WT. | LEVEL OF SIGNIFICANCE |
|---|---|---|---|---|
| 1 | 200 | 162 | −19 | .005 |
| 1 | 163 | 179 | +10 | .07 |
| 2 | 146 | 176 | +21 | .005 |
| 3 | 181 | 217 | +20 | .005 |
| 2 | 124 | 148 | +19 | .06 |

TABLE 3

Increases in Water Uptake of 14-Day Old Hybrid Sweet Corn ("Silver Queen") Sprayed with 100 μ/l Triacontanol Using Different Formulations without 15-30-15 Fertilizer.

| FORMULATION | AVERAGE WATER WT. (mg/shoot) CONTROL | AVERAGE WATER WT. (mg/shoot) $C_{30}H_{61}OH$ | PERCENT INCREASE IN WATER WT. | LEVEL OF SIGNIFICANCE |
|---|---|---|---|---|
| 1 | 1731 | 1209 | −30% | .005 |
| 2 | 1560 | 1800 | −15% | .005 |

TABLE 4

Increases in Water Uptake of 14-Day Old Hybrid Sweet Corn ("Silver Queen") Sprayed with 100 μ/l Triacontanol Using Different Formulations with 15-30-15 Fertilizer.

| FORMULATION | AVERAGE WATER WT. (mg/shoot) CONTROL | AVERAGE WATER WT. (mg/shoot) $C_{30}H_{61}OH$ | PERCENT INCREASE IN WATER WT. | LEVEL OF SIGNIFICANCE |
|---|---|---|---|---|
| 1 | 1790 | 1638 | −8 | .05 |
| 1 | 1535 | 1410 | −10 | .07 |
| 2 | 1584 | 1834 | +16 | .005 |
| 3 | 1391 | 1470 | +6 | N.S. |
| 2 | 1342 | 1727 | +29 | .02 |

TABLE 5

Increases in Dry Weight and Water Uptake of 14-Day Old Corn Plants Sprayed with a Variety of Plant Growth Substances with and without 1-Triacontanol On day 7.

| Additive Cmpd | Conc.(M) | Triacontanol (100 μg/l) | Formulation | Increases Dry Wt. | Water Uptake |
|---|---|---|---|---|---|
| Sweet Corn | | | | | |
| IAA | $10^{-5}$ | NO | 4 | +4% | −7% |
| IAA | $10^{-5}$ | YES | 4 | +2% | −5% |
| $GA_3$ | $10^{-5}$ | NO | 2 | −24 | −6 |
| $GA_3$ | $10^{-5}$ | YES | 2 | −15 | −3 |
| Kinetin | $10^{-5}$ | NO | 5 | −24 | −3 |
| Kinetin | $10^{-5}$ | YES | 5 | −21 | +14 |
| 2,4-D | $10^{-5}$ | NO | 4 | +10 | −9 |
| 2,4-D | $10^{-5}$ | YES | 4 | +17 | −13 |
| TIBA | $10^{-4}$ | NO | 4 | +10 | −12 |
| TIBA | $10^{-4}$ | YES | 4 | +19 | +1 |
| MH | $10^{-4}$ | NO | 4 | +7 | −1 |
| MH | $10^{-4}$ | YES | 4 | +12 | −7 |
| $CaCl_2$ | $10^{-2}$ | NO | 2 | +4 | −2 |
| $CaCl_2$ | $10^{-2}$ | YES | 2 | +65 | +11 |
| $LaCl_3$ | $10^{-2}$ | NO | 2 | +5 | −2 |
| $LaCl_3$ | $10^{-2}$ | YES | 2 | +72 | +18 |
| $Ce(SO_4)_2$ | $10^{-3}$ | YES | 2 | +21 | +26 |
| $MgCl_2$ | $10^{-3}$ | YES | 2 | +21 | +20 |
| $MnCl_2$ | $10^{-3}$ | YES | 2 | +9 | +29 |
| $MgCl_2 + CaCl_2$ | $10^{-3}$ | YES | 2 | +39 | +30 |
| — | — | YES | 2 | +20 | +16 |
| Field Corn | | | | | |
| $CaCl_2 + MgCl_2$ | $10^{-3}$ ea. | YES | 2 | +20-30 | +21 |
| $LaCl_3$ | $10^{-3}$ | YES | 2 | +25-32 | +25 |
| $CaCl_2$ | $10^3$ | YES | 2 | +20-30 | +6-18 |

As shown in Table 5, the 1-triacontanol formulations, without metal ions, increased the dry weight and water uptake of Sweet Corn about 20% and 16%, respectively. However, when $CaCl_2$ and $LaCl_3$ were added to the formulations, the dry weights increases were up to 65% and 72%, respectively. It is therefore clear that metal ions significantly increase the plant growth stimulating effects of 1-triacontanol.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A plant growth stimulator formulation, consisting essentially of:
an effective plant growth stimulating amount of 1-triacontanol; a water soluble or miscible polar organic solvent in which 1-triacontanol is soluble; metal ions selected from the group consisting of $Ca^{++}$ and $La^{+3}$, said metal ions being present in an amount effective to assist the 1-triacontanol in stimulating plant growth; and water.

2. A formulation according to claim 1, wherein said metal ions are $Ca^{++}$.

3. A formulation according to claim 1, wherein said metal ions are $La^{+3}$.

4. A formulation according to claim 1, wherein said metal ions are present in a concentration of between about $10^{-1}$ and $10^{-5}$ Molar.

5. A formulation according to claim 1, wherein said metal ions are present in a concentration of between about $10^{-2}$ and $10^{-4}$ Molar.

6. A formulation according to claim 1, wherein said polar organic solvent is selected from the group consisting of alcohols, ketones, water soluble ethers, glycols and organic carboxylic acids.

7. A formulation according to claim 1, wherein said polar organic solvent is selected from the group consisting of acetone, methyl ethyl ketone, methanol, ethanol, isopropanol, diethylene glycol, n-butanol, propylene glycol, dioxane and acetic acid.

8. A formulation according to claim 1, wherein said solvent is a ketone.

9. A formulation according to claim 1, wherein said solvent is acetone.

10. A formulation according to claim 1, wherein said metal ions are dissolved in said formulation as metal salts.

11. A formulation according to claim 1, wherein said metal salts are inorganic metal salts.

12. A formulation according to claim 10, wherein said metal salt is $CaCl_2$.

13. A formulation according to claim 1, having a pH of 7 or greater.

14. A method for stimulating the growth of corn plants, comprising the steps of:
spraying an effective plant growth stimulating amount of the composition of claim 1 onto the leaves of the growing corn plants.

15. A method according to claim 14, wherein the spraying is done when the plant has 2 or 3 true leaves.

16. A method for stimulating the growth of corn plants, comprising the steps of:
spraying an effective plant growth stimulating amount of the composition of claim 2, 3, 4, 5, 8, 9, 11, 12 or 13 onto the leaves of the growing corn plant.

* * * * *